(12) United States Patent
Guan (10) Patent No.: US 10,201,677 B2
(45) Date of Patent: Feb. 12, 2019

(54) ENDOTRACHEAL TUBE COMPRISING PHARYNGEAL SUCTION CATHETER

(71) Applicant: Kaipan Guan, Guangzhou (CN)

(72) Inventor: Kaipan Guan, Guangzhou (CN)

( * ) Notice: Subject to any disclaimer, the term of this patent is extended or adjusted under 35 U.S.C. 154(b) by 0 days.

(21) Appl. No.: 15/571,459

(22) PCT Filed: Nov. 12, 2015

(86) PCT No.: PCT/CN2015/094413
§ 371 (c)(1),
(2) Date: Nov. 2, 2017

(87) PCT Pub. No.: WO2017/024681
PCT Pub. Date: Feb. 16, 2017

(65) Prior Publication Data
US 2018/0126106 A1 May 10, 2018

(30) Foreign Application Priority Data
Aug. 10, 2015 (CN) .......................... 2015 1 0486059

(51) Int. Cl.
*A61M 16/04* (2006.01)

(52) U.S. Cl.
CPC ........ *A61M 16/0463* (2013.01); *A61M 16/04* (2013.01); *A61M 16/0477* (2014.02); *A61M 16/0409* (2014.02); *A61M 16/0488* (2013.01)

(58) Field of Classification Search
CPC .............. A61M 16/04; A61M 16/0463; A61M 16/0477; A61M 16/0488; A61M 16/0409
See application file for complete search history.

(56) References Cited

U.S. PATENT DOCUMENTS 5,067,497 A * 11/1991 Greear ................ A61M 16/04
128/207.15
6,460,540 B1 10/2002 Klepper
(Continued)

FOREIGN PATENT DOCUMENTS

CN 202270240 U 6/2012
CN 202342638 U 7/2012
(Continued)

OTHER PUBLICATIONS

Communication from a foreign patent office in a counterpart foreign application, The State Intellectual Proerpty Office of People's Republic of China, "First Office Action," Chinese Application No. 201510486059.0, dated Nov. 17, 2016, 24 pages.

*Primary Examiner* — Gregory Anderson
*Assistant Examiner* — Margaret Luarca (57) ABSTRACT

Provided is an endotracheal tube, which comprises a baffle, an endotracheal tube body and a pharyngeal suction catheter and is integrally formed. The pharyngeal suction catheter is fixedly connected with an outer wall of the endotracheal tube body. One end of the pharyngeal suction catheter is bent to form a front bent portion, a port of the front bent portion is closed and a side wall of the front bent portion is provided with two suction ports. In the case of oral endotracheal intubation, the pharyngeal suction catheter is introduced to the bottom of the pharynx as the endotracheal tube body is inserted into the weasand, and the pharyngeal suction catheter can stay there for a long period of time, enabling high efficiency of removal of pharyngeal secretions, the reduction of discomfort and adsorption injury of the patient, and the reduction of nursing workload.

13 Claims, 5 Drawing Sheets

(56) References Cited

U.S. PATENT DOCUMENTS

| | | | |
|---|---|---|---|
| 2002/0014238 A1* | 2/2002 | Kotmel | A61M 16/04 128/204.18 |
| 2007/0113844 A1 | 5/2007 | Garren et al. | |
| 2009/0125002 A1* | 5/2009 | Totz | A61M 16/04 604/528 |
| 2010/0152706 A1* | 6/2010 | Morris | A61M 1/008 604/523 |
| 2014/0316207 A1 | 10/2014 | Hain | |
| 2016/0235934 A1* | 8/2016 | Poulsen | A61M 16/0409 |

FOREIGN PATENT DOCUMENTS

| | | |
|---|---|---|
| CN | 202459706 U | 10/2012 |
| CN | 202459708 U | 10/2012 |
| CN | 103656813 A | 3/2014 |
| CN | 204890871 U | 12/2015 |

\* cited by examiner

ENDOTRACHEAL TUBE COMPRISING PHARYNGEAL SUCTION CATHETER

CROSS-REFERENCE TO RELATED APPLICATIONS

The present application claims priority under 35 U.S.C. § 365 and is a 371 National Stage of International Application No. PCT/CN2015/094413 filed Nov. 12, 2015, which claims the benefit of Chinese Patent Application No. 201510486059.0 filed Aug. 10, 2015, the disclosures of which are fully incorporated herein by reference into the present disclosure as if fully set forth herein.

TECHNICAL FIELD

The present disclosure relates to the technical field of medical apparatuses, and particularly to an endotracheal tube with a pharyngeal suction catheter.

BACKGROUND

The ventilator assisted breathing after endotracheal intubation is the main clinical measure adopted to treat respiratory failure, severe heart failure and surgical anesthesia. However, endotracheal intubation often induces ventilator-associated pneumonia, which may prolong the hospitalization time of a patient, increase the hospitalization cost, and may even lead to an increase in mortality. Ventilator-associated pneumonia often results from infection with multiple drug-resistant bacteria, and has become a medical problem. There are many causes for incidence of ventilator-associated pneumonia after endotracheal intubation, among others, the inhalation of secretions from the oral cavity, the pharynx and the nose is the most primary factor. Therefore, preventing secretions of the oral cavity, the pharynx and the nose from entering the lung can significantly reduce the incidence of ventilator-associated pneumonia.

At present, the main measures taken in clinical practice include: (1) periodic or sustained suction under the glottis; (2) on-demand or periodic suction of secretions from the oral cavity and the pharynx with a sputum suction tube; (3) periodic cleaning of the oral cavity and the pharynx; and (4) periodic monitoring of the balloon pressure, with the pressure maintained at a water column level of 20 to 30 cm. However, these measures have poor effects and cannot effectively prevent pharyngeal secretions from entering the lung, thereby causing the incidence of ventilator-associated pneumonia to be remained high. At present, suction with a sputum suction tube conventionally used in clinical practice is easy to cause mucosal injury and bleeding, and has a poor cleaning effect. In addition, the existing measures require quite cumbersome operations and large nursing workload.

SUMMARY

An object of the present disclosure is to provide an endotracheal tube with a pharyngeal suction catheter, which makes a suction operation simple and efficient, reduces the side effects caused by a conventional suction operation with the use of a sputum suction tube, greatly improves the efficiency of removal of pharyngeal secretions, and attains the purpose of reducing the incidence of ventilator-associated pneumonia.

The present disclosure is achieved as follows.

Provided is an endotracheal tube with a pharyngeal suction catheter, the endotracheal tube includes a endotracheal tube body and a pharyngeal suction catheter, with the pharyngeal suction catheter configured for sucking and removing pharyngeal secretions from a patient. The endotracheal tube body is formed integrally with the pharyngeal suction catheter, and the pharyngeal suction catheter is connected with an outer wall of the endotracheal tube body and fixed directly behind the endotracheal tube body.

In one embodiment, the endotracheal tube further includes a baffle, the baffle is sleeved onto one end of the endotracheal tube body, and the baffle is located at a position higher than a balloon of the endotracheal tube body by 3.5 cm.

The baffle may offer the following functions: in one aspect, the baffle avoids secretions of the oral cavity from flowing into the patient's glottis along the endotracheal tube body; and in another aspect, the baffle also has a function of positioning. Specifically, after the endotracheal tube is successfully inserted into the glottis, the tube body is pushed gently forward so that the baffle abuts gently against the laryngeal aperture, and then the tube body is rotated so that a front bent portion of the pharyngeal suction catheter is directed perpendicularly towards a posterior pharyngeal wall, and therefore, a port of the pharyngeal suction catheter is confined at a position located at the bottom of the pharynx of the patient, such that liquids accumulated in the pharynx are sucked more thoroughly through the pharyngeal suction catheter.

In one embodiment, the endotracheal tube further includes a first flushing tube. The first flushing tube is embedded in a front wall of the endotracheal tube body. One end of the first flushing tube is provided with an opening, with the opening toward outside of the endotracheal tube body and distanced from the baffle by 1.5 cm. The first flushing tube runs along with the endotracheal tube body to go beyond a incisor line, and is separated, after being away from the incisor line by 3.0 cm, from the endotracheal tube body. The first flushing tube is extended so as to be externally connected with a syringe connector. The first flushing tube is used for flushing the laryngopharynx of the patient.

In one embodiment, one end of the pharyngeal suction catheter is located adjacent to the baffle. The pharyngeal suction catheter runs along with the endotracheal tube body and is separated, at a position 3.5 cm lower than the incisor line by 3.5 cm, from the endotracheal tube body. The pharyngeal suction catheter is extended so as to be externally connected with a hose connector. This facilitates the connection with a suction apparatus, and facilitates the fixation of the endotracheal tube.

In one embodiment, one end of the pharyngeal suction catheter, which is adjacent to the baffle, is bent arcuately downward and rearward in a direction away from the endotracheal tube body to form a front bent portion. The front bent portion is perpendicular to the endotracheal tube body, a port of the front bent portion is distanced from the endotracheal tube body by 1.2 cm, and an end of the front bent portion is flush with a level line of the baffle. The pharyngeal suction catheter is provided with the front bent portion, and after the endotracheal tube is successfully inserted into the trachea of the patient and is fixed, the front bent portion enables the port of the pharyngeal suction catheter to be closer to the mucosa of the posterior pharyngeal wall of the patient, so as to perform the suction more thoroughly.

In one embodiment, the port of the front bent portion is closed, a side wall of the front bent portion is provided with two suction ports, the two suction ports are symmetrically distributed along an axial direction of the pharyngeal suction catheter, and both of the suction ports are distanced from the end of the front bent portion by 3 mm. With the above design of the end of the pharyngeal suction catheter, the suction port is kept at a distance from the mucosa, thereby avoiding or reducing adsorption injury that is caused by the suction port to the mucosa of the pharynx of the patient, so as to avoid the problem of mucosal bleeding.

In one embodiment, the endotracheal tube further includes a second flushing tube. The second flushing tube is embedded in a front wall of the pharyngeal suction catheter connected with the endotracheal tube body. An opening of one end of the second flushing tube is disposed in a catheter cavity and located below and behind the suction ports on both sides, and the opening is close to the port of the pharyngeal suction catheter. The second flushing tube runs along with the pharyngeal suction catheter to go beyond the incisor line and is separated, after being away from the incisor line by 3.0 cm, from the pharyngeal suction catheter. The second flushing tube is extended so as to be externally connected with a syringe connector. The second flushing tube not only enables the suction ports and the catheter cavity of the pharyngeal suction catheter to be flushed so as to keep them unobstructed, but also enables the mucosa at the bottom of the pharynx to be flushed.

In one embodiment, the endotracheal tube further includes a humidity sensing device. The humidity sensing device includes a connecting wire and a humidity sensing electrode. The humidity sensing electrode is disposed at the side wall of the front bent portion and located beside the port of the front bent portion. One end of the connecting wire is electrically connected with the humidity sensing electrode, and the other end of the connecting wire protrudes out of an oral cavity of the patient. The humidity sensing electrode may sense an ambient humidity of the patient's pharynx. In the case where a certain amount of secretions are accumulated at the patient's pharynx, the humidity sensing electrode may transmit this information to an external device, so that the doctor can suck the secretions in time, so as to achieve the suction of the pharyngeal secretions as needed. Therefore, it is possible to reduce overflow of the pharyngeal secretions into the glottis, and attain the purpose of reducing ventilator-associated pneumonia.

In one embodiment, the endotracheal tube further includes a third flushing tube. The third flushing tube is embedded in a rear tube wall of the pharyngeal suction catheter. One end of the third flushing tube directly faces a top of a hard palate of the patient after successful intubation of the patient, and the one end of the third flushing tube is provided with an opening, with the opening toward outside of the rear tube wall. The third flushing tube runs along with the pharyngeal suction catheter to go beyond the incisor line and is separated, after being away from the incisor line by 3.0 cm, from the pharyngeal suction catheter. The third flushing tube is extended so as to be externally connected with a syringe connector. The third flushing tube can be utilized to flush the patient's oral cavity, to keep the oral cavity clean and prevent breeding of bacteria in the oral cavity.

In one embodiment, the endotracheal tube further includes a silicone film formed integrally with the endotracheal tube body and the pharyngeal suction catheter. The silicone film is connected with each of an outer side wall of the pharyngeal suction catheter and an outer side wall of the endotracheal tube body. The silicone film, the outer side wall of the pharyngeal suction catheter and the outer side wall of the endotracheal tube body constitute a gastric tube tunnel through which a gastric tube can pass. The silicone film is located beside the pharyngeal suction catheter and behind the endotracheal tube body. A tunnel cavity of the gastric tube tunnel has a size sufficient such that a conventional gastric tube can pass through. An opening of one end of the gastric tube tunnel is distanced from the baffle by 4.0 cm, and an opening of the other end of the gastric tube tunnel protrudes out of an oral cavity of the patient. The endotracheal tube is provided with the gastric tube tunnel; in this case, after the endotracheal tube is successfully inserted into the patient, it is easier to insert a gastric tube through the gastric tube tunnel, and there is no need to suspend the gastric tube in the nasal cavity, thereby reducing the incidence of discomfort of the nasal cavity, mucosal injury and bleeding as well as sinusitis.

Beneficial effects of the present disclosure:

Embodiments of the present disclosure provide an endotracheal tube with a pharyngeal suction catheter. The endotracheal tube includes an endotracheal tube body and a pharyngeal suction catheter formed integrally. The pharyngeal suction catheter is inserted along with the insertion of the endotracheal tube. During the indwelling of the endotracheal tube, the pharyngeal suction catheter can be positioned and indwelled for a long time, which achieves high efficiency of the suction and removal of pharyngeal secretions from the patient, and significantly relieves the problem that the secretions at the bottom of the pharynx overflow into the glottis or flow into the glottis along the endotracheal tube. By providing the pharyngeal suction catheter with a bent end, a closed port and suction ports at the side wall as well as by providing the flushing tubes, the efficiency of removal of pharyngeal secretions is improved, and at the same time, the side effects of the conventional suction are reduced, the oral cavity and the pharynx are kept clean, and the mucosa is kept moist.

BRIEF DESCRIPTION OF THE DRAWINGS

For illustrating technical solutions of embodiments of the present disclosure more clearly, drawings required for use in the embodiments will be introduced briefly below. It is to be understood that the drawings below are merely illustrative of some embodiments of the present disclosure, and therefore should not to be considered as limiting its scope.

DESCRIPTION OF REFERENCE NUMERALS endotracheal tube body 101; first flushing tube 102; pharyngeal suction catheter 103; balloon inflation tube 104; baffle 105; balloon 106; side wall opening 107; tip opening 108; distal opening 109; suction catheter above balloon 110;

opening of suction catheter above balloon 111; front bent portion 201; suction port 202; third flushing tube 301; second flushing tube 302; connecting wire 401; silicone film 402; and humidity sensing electrode 403.

DETAILED DESCRIPTION

In order to make the objects, technical solutions and advantages of the embodiments of the present disclosure more clear, the technical solutions of the embodiments of the present disclosure will be described below clearly and completely with reference to the drawings of the embodiments of the present disclosure. It is apparent that the embodiments to be described are some, but not all of the embodiments of the present disclosure. Generally, the components of the embodiments of the present disclosure, as described and illustrated in the figures herein, may be arranged and designed in various different configurations. Thus, the following detailed description of the embodiments of the present disclosure, as represented in the figures, is not intended to limit the scope of the present disclosure as claimed, but is merely representative of selected embodiments of the present disclosure. All the other embodiments obtained by those skilled in the art in light of the embodiments of the present disclosure without inventive efforts would fall within the scope of the present disclosure as claimed.

It should be noted that similar reference numerals and letters refer to similar items in the following figures, and thus once an item is defined in one figure, it may not be further defined or explained in the subsequent figures.

In the description of the present disclosure, it should be indicated that orientation or positional relations indicated by terms such as "center", "up", "down", "left", "right", "vertical", "horizontal", "inside", "outside" and "middle" are based on the orientation or positional relations as shown in the drawings, or the orientation or positional relations in which the inventive product is conventionally placed in use, and these terms are intended only to facilitate the description of the present disclosure and simplify the description, but not intended to indicate or imply that the referred devices or elements must be in a particular orientation or constructed or operated in the particular orientation, and therefore should not be construed as limiting the present disclosure. In addition, terms such as "first", "second" and "third" are used only for distinguishing the description, and should not be understood as indicating or implying to have importance in relativity.

In the description of the present disclosure, it should also be indicated that, unless otherwise expressly specified or defined, terms "provide", "mount", "couple" and "connect" should be understood in a broad sense. For example, connection may be fixed connection or detachable connection or integral connection, may be mechanical connection or electric connection, or may be direct coupling or indirect coupling via an intermediate medium, or may be internal communication between two elements. The specific meanings of the above-mentioned terms in the present disclosure could be understood by those skilled in the art according to specific situations.

Referring to FIGS. 1-6, various embodiments may provide an endotracheal tube with a pharyngeal suction catheter 103. The endotracheal tube includes an endotracheal tube body 101 and a pharyngeal suction catheter 103, with the pharyngeal suction catheter configured for sucking pharyngeal secretions from a patient. The endotracheal tube body 101 is formed integrally with the pharyngeal suction catheter 103. The pharyngeal suction catheter 103 is connected to an outer wall of the endotracheal tube body 101, and is fixed directly behind the endotracheal tube body 101 (which refers to a placement position in the case where the patient, for whom the endotracheal tube has been successfully inserted and fixed, is in a supine position, with the position of the head corresponding to an upper position, the position of the foot corresponding to a lower position, the nose located at the front, and the pillow located at the rear). In some embodiments, the diameter of the pharyngeal suction catheter is equivalent to the diameter of a sputum suction tube F16, and is about 5.33 mm.

Figure 1:
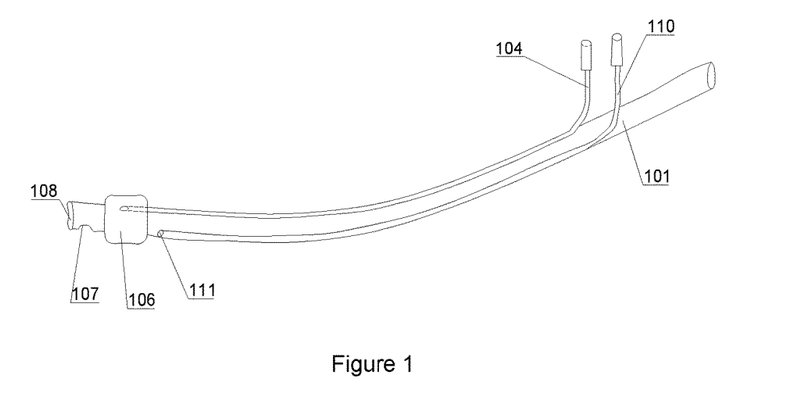
FIG. 1 illustrates a schematic structural view of a common endotracheal tube currently used in clinical practice.

The main part of the endotracheal tube has no difference from a common endotracheal tube currently used in clinical practice. As shown in FIG. 1, one end of the endotracheal tube body 101 is provided with a balloon 106 and a balloon inflation tube 104, with the balloon inflation tube configured for inflating the balloon with gas. The endotracheal tube body 101 of an arc shape is provided with a tip opening 108, and a side wall opening 107 is provided on a side wall of the endotracheal tube body 101 at a position adjacent to the tip opening 108. The endotracheal tube body 101 is further provided with a suction catheter above balloon 110, and an opening of suction catheter above balloon 111, located at one end of the suction catheter above balloon, is adjacent to the balloon 106. The endotracheal tube body 101 is marked with a scale mark.

The pharyngeal suction catheter 103 is disposed on the endotracheal tube, and the pharyngeal suction catheter 103 is utilized to suck and remove the secretions accumulated at the bottom of the pharynx of the patient. In the case of peroral endotracheal intubation, the endotracheal tube body 101 enters the trachea of the patient, and meanwhile, the pharyngeal suction catheter 103 is also inserted into the patient's laryngopharynx. Thus, during the indwelling of the endotracheal tube, the pharyngeal suction catheter 103 can be kept indwelling in the patient's laryngopharynx, and the doctor may suck the secretions through a distal opening 109 of the pharyngeal suction catheter 103 as needed. Since the pharyngeal suction catheter 103 indwells in the patient's laryngopharynx all the time, there is no need to carry out the suction with a current conventional method which has to make a sputum suction tube frequently inserted into and withdrawn from the pharynx for suction, thereby reducing the pain as well as mucosal injury and bleeding which are caused to the patient.

One end of the pharyngeal suction catheter 103 is located adjacent to a baffle, so as to suck and remove the secretions from the pharynx. The pharyngeal suction catheter runs along with the endotracheal tube body, and is separated, at a position lower than the incisor line by 3.5 cm, from the endotracheal tube body. The pharyngeal suction catheter is extended to protrude out of the patient's oral cavity, so as to be externally connected with a hose connector. The pharyngeal suction catheter 103 is separated, at the position lower than the incisor line by 3.5 cm, from the endotracheal tube body 101, that is, the pharyngeal suction catheter 103 and the endotracheal tube body 101 are relatively independent of each other in the vicinity of the incisor line. Therefore, this can further facilitate the connections with various apparatuses and the fixation of the endotracheal tube body 101, and prevent the normal fixation of the endotracheal tube body 101 from being affected, where such affection would be produced in the case where the pharyngeal suction catheter 103 and the endotracheal tube body 101 are still joined together at the position of the incisor line.

Figure 2:
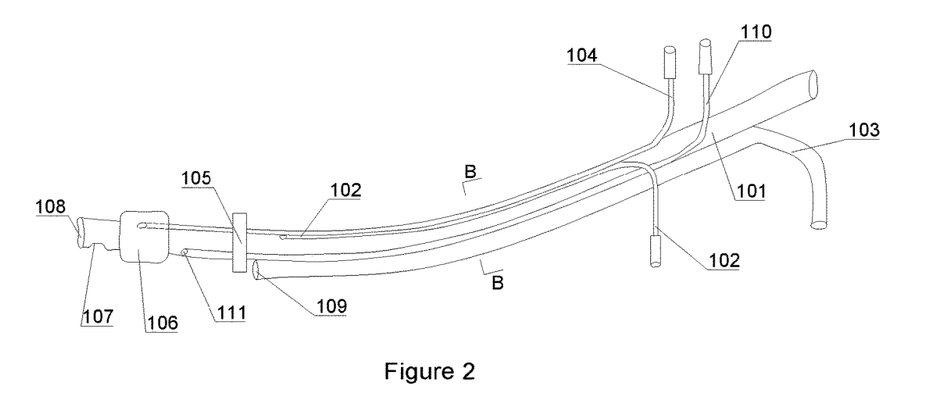
FIG. 2 illustrates a schematic structural view of an endotracheal tube with a pharyngeal suction catheter in accordance with various embodiments of the present disclosure.
Figure 3:
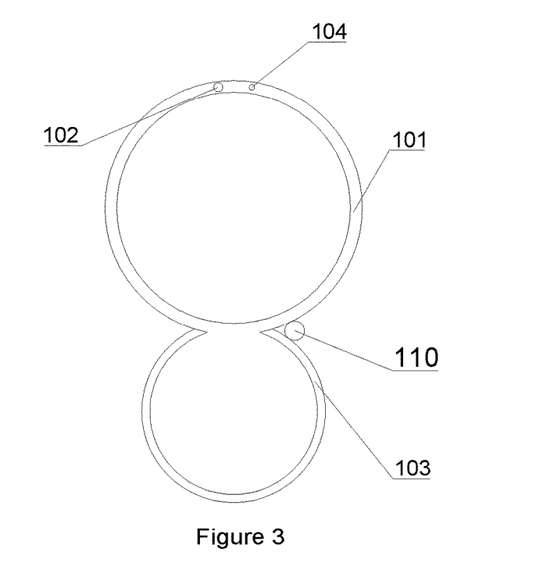
FIG. 3 illustrates a schematic sectional view of a B-B plane in FIG. 2.
Figure 4:
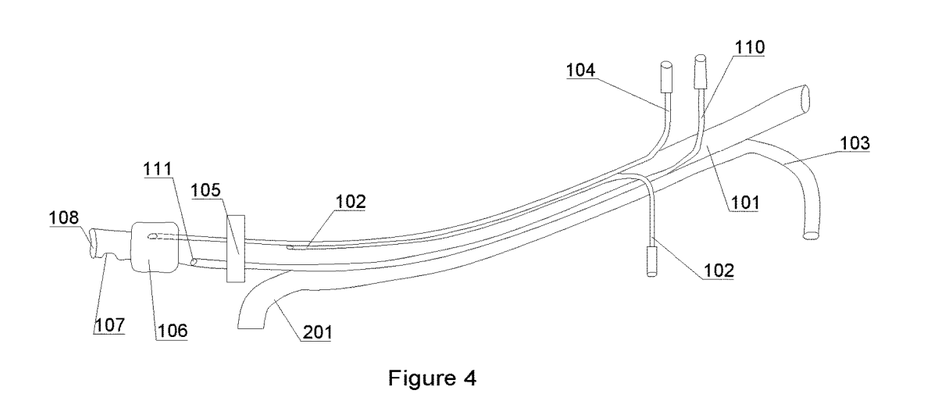
FIG. 4 illustrates a schematic structural view of the endotracheal tube with the pharyngeal suction catheter in accordance with various embodiments of the present disclosure, with the pharyngeal suction catheter having a front bent portion.
Figure 5:
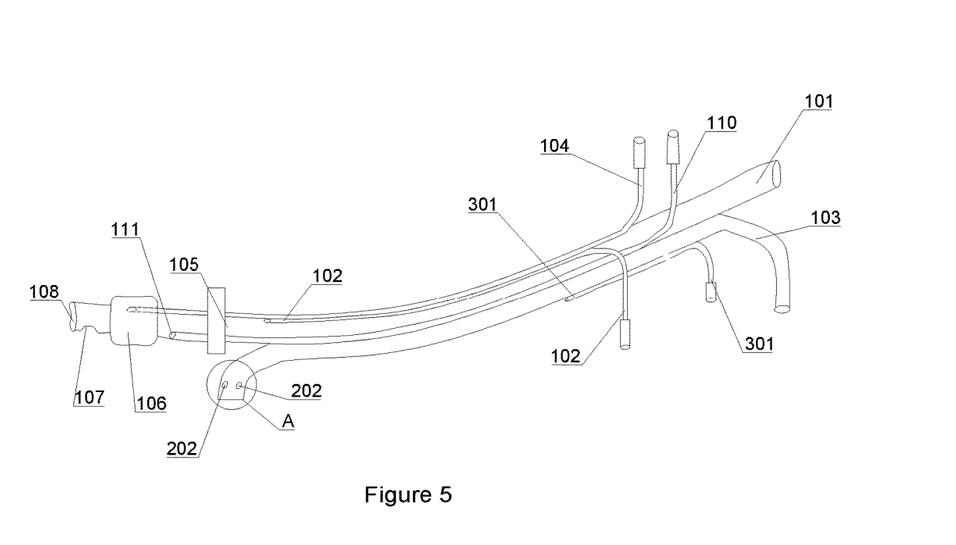
FIG. 5 illustrates a schematic structural view of an endotracheal tube with a pharyngeal suction catheter in accordance with various embodiments of the present disclosure.
Figure 6:
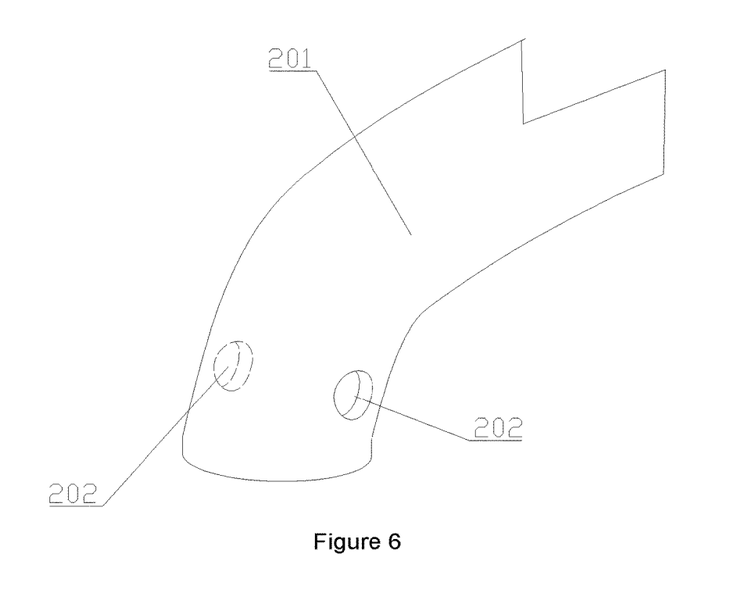
FIG. 6 illustrates an enlarged view of part A in FIG. 5.

The distal opening 109 of the pharyngeal suction catheter 103 shown in FIG. 2 is too far away from the posterior pharyngeal wall; and thus, it is difficult to effectively suck and remove a small amount of accumulated pharyngeal secretions, in the case where the patient is conventionally in a supine position with his/her head raised by 30 degrees. Therefore, a design may be adopted with one end of the pharyngeal suction catheter 103, which is adjacent to the baffle, bent arcuately downward and rearward in a direction away from the endotracheal tube body 101 to form a front bent portion 201. The front bent portion 201 is perpendicular to the endotracheal tube body 101, a port of the front bent portion is distanced from the endotracheal tube body by 1.2 cm, and an end of the front bent portion 201 is disposed at a position flush with a level line of the baffle. After the endotracheal tube is successfully inserted, and when the patient is in the supine position with his/her head raised by 30 degrees, the front bent portion 201 is directed perpendicularly towards the patient's posterior pharyngeal wall, and the port of the suction catheter will be naturally close to the lowest part of the bottom of the pharynx, so that the secretions are removed more thoroughly. In addition, since the end of the front bent portion 201 (i.e., the distal opening 109) is very close to the pharyngeal mucosa of the patient, it is easy for the opening to cause adsorption injury to the mucosa when the secretions are sucked and removed through the distal opening 109 provided at the front bent portion. In view of the above situation, the port of the front bent portion 201 is closed, that is, the distal opening 109 is closed, and openings are provided on a side catheter wall of the front bent portion. That is, the side wall of the front bent portion 201 is provided with two suction ports 202. The two suction ports 202 are symmetrically distributed along an axial direction of the pharyngeal suction catheter 103, and the two suction ports 202 are distanced from the end of the front bent portion 201 by 3 mm. In this way, during the suction of the secretions, the port of the front bent portion 201 does not have an adsorption effect on the mucosa of the pharynx, and the pharyngeal suction catheter 103 sucks and removes the secretions by generating a suction action through the suction ports 202 located in the side wall of the front bent portion 201. Moreover, the suction ports located in the side wall of the front bent portion 201 are away from the mucosa by a certain distance and are blocked by the end of the front bent portion 201, thus the suction ports 202 in the side wall does not have an adsorption effect on the mucosa of the pharynx as well, and the adsorption injury of the mucosa can be avoided.

The endotracheal tube with the pharyngeal suction catheter 103 may further include the baffle. The baffle 105 is sleeved onto one end of the endotracheal tube body 101. The baffle is located above the balloon of the endotracheal tube body, and the baffle 105 is distanced from the balloon 106 of the endotracheal tube by 3.5 cm. The baffle is of a circular ring shape, is about 0.35 to 0.40 cm greater than the endotracheal tube body 101, and a thickness of the baffle is about 0.30 to 0.35 cm. The baffle may be made of a soft silicone material, to avoid damage to the mucosa which would otherwise be caused if the material of the baffle has an excessive hardness. After the endotracheal tube is successfully inserted, the baffle 105 can prevent the secretions of the oral cavity from flowing into the glottis along the endotracheal tube body 101, so as to reduce the occurrence of inhalation. In addition, after the endotracheal tube is successfully inserted into the glottis, the tube body is pushed gently forward so that the baffle 105 abuts gently against the laryngeal aperture, which indicates that the endotracheal tube has been inserted to a designated position. At this point, the tube body is rotated so that the front bent portion of the pharyngeal suction catheter is directed perpendicularly towards the posterior pharyngeal wall, and the inflation pressure of the inflated balloon is adjusted to a level of around 20 to 30 cm, so as to preliminarily determine the intubation depth. In this way, the pharyngeal suction catheter may be positioned so that the end of the pharyngeal suction catheter 103 is located at the bottom of the pharynx, so as to more effectively and thoroughly suck and remove the secretions accumulated at the bottom of the pharynx. In order to conveniently control the angle by which the endotracheal tube is rotated, the endotracheal tube is further provided with a black mark line. The black mark line is disposed at the tail section of the endotracheal tube body and located on a median line of the front tube wall of the endotracheal tube body, and one end of the black mark line is located at a position 3.0 cm ahead of the incisor line. After the endotracheal tube is successfully inserted into the glottis, the tube body is pushed gently forward so that the baffle abuts gently against the laryngeal aperture, and then the tube body is rotated so that the front bent portion of the pharyngeal suction catheter is directed perpendicularly towards the posterior pharyngeal wall, and therefore the port of the pharyngeal suction catheter is confined at a position located at the bottom of the pharynx of the patient. After the balloon is inflated, the endotracheal tube body is preliminarily fixed; and finally, when the fixation is made round the mouth, the mark line is positioned to be in the direction of the median line, and the intubation depth is recorded.

In order to keep the patient's pharynx clean, the endotracheal tube further includes a first flushing tube 102. The first flushing tube 102 is embedded in the front wall of the endotracheal tube body 101. One end of the first flushing tube 102 is provided with an opening, with the opening toward outside of the endotracheal tube body and distanced from an upper edge of the baffle by 1.5 cm. The first flushing tube 102 runs along with the endotracheal tube body 101 to go beyond the incisor line, and is separated, after being away from the incisor line by 3.0 cm, from the endotracheal tube body 101. The other end of the first flushing tube is extended so as to be externally connected with a syringe connector. The first flushing tube 102 is used to flush the patient's laryngopharynx to keep it clean and moist.

Figure 7:
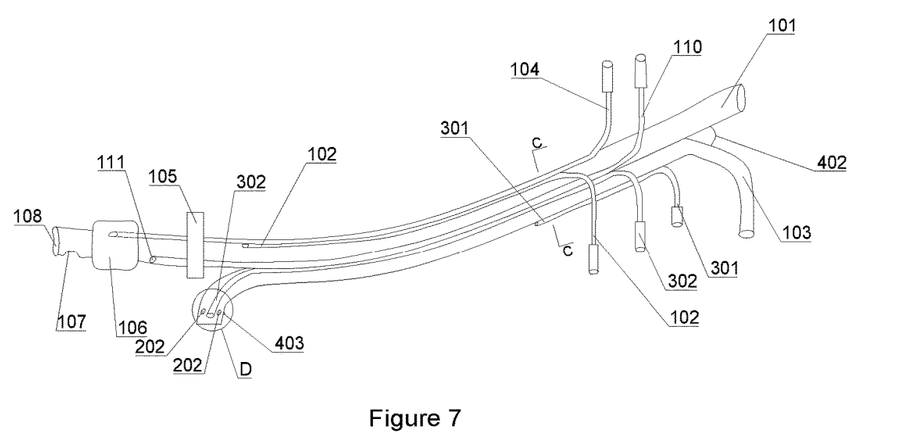
FIG. 7 illustrates a schematic structural view of another endotracheal tube with a pharyngeal suction catheter in accordance with various embodiments of the present disclosure.
Figure 8:
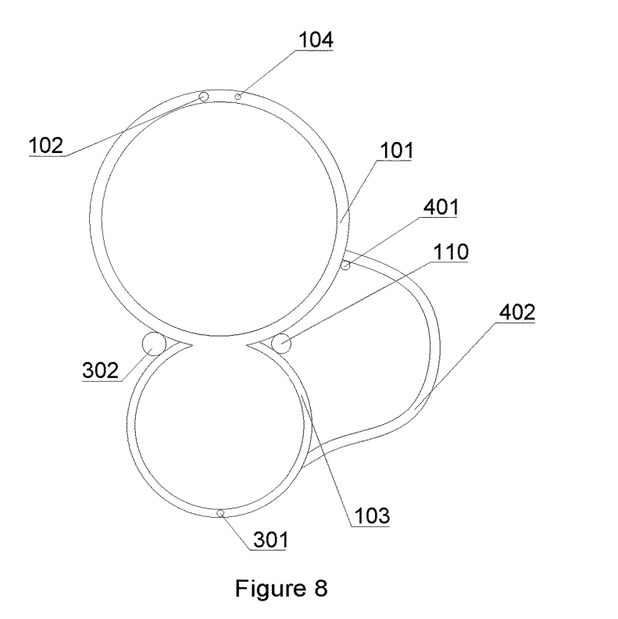
FIG. 8 illustrates a schematic sectional view of the C-C plane in FIG. 7.
Figure 9:
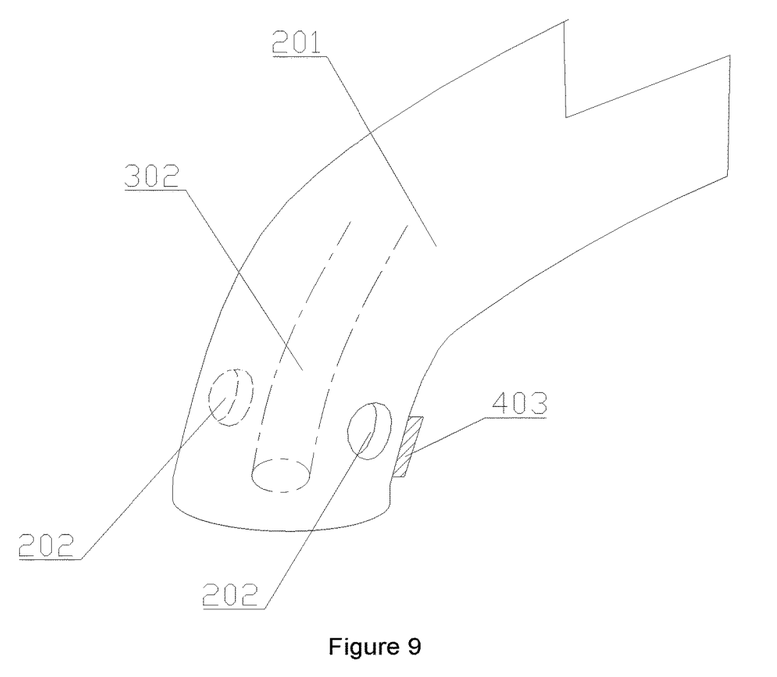
FIG. 9 illustrates an enlarged view of part D in FIG. 7.

Referring to FIGS. 7-9, the endotracheal tube with the pharyngeal suction catheter 103 further includes a second flushing tube 302. The second flushing tube 302 is embedded in the front wall of the pharyngeal suction catheter 103 connected with the endotracheal tube body 101. An opening of one end of the second flushing tube 302 is disposed in a catheter cavity and located below and behind the suction ports 202 on both sides, and this opening is close to the port of the pharyngeal suction catheter 103 (i.e., the port of the front bent portion). The second flushing tube 302 runs along with the pharyngeal suction catheter 103 to go beyond the incisor line, and is separated, after being away from the incisor line by 3.0 cm, from the pharyngeal suction catheter 103. The second flushing tube is extended so as to be externally connected with a syringe connector. The second flushing tube 302 enables the suction ports and the catheter cavity of the pharyngeal suction catheter 103 to be flushed so as to keep them unobstructed, and moreover, the second flushing tube can also enable the bottom of the pharynx of the patient to be flushed to keep the bottom of the pharynx clean.

Furthermore, the endotracheal tube with the pharyngeal suction catheter 103 further includes a third flushing tube 301. The third flushing tube 301 is embedded in a rear tube wall of the pharyngeal suction catheter 103. One end of the third flushing tube 301 directly faces the top of the hard palate of the patient after the successful intubation of the patient, and this end is provided with an opening, with the opening toward outside of the rear tube wall. The third flushing tube 301 runs along with the pharyngeal suction catheter 103 to go beyond the incisor line, and is separated, after being away from the incisor line by 3.0 cm, from the pharyngeal suction catheter 103. The third flushing tube is extended so as to be externally connected with a syringe connector. The oral cavity of the patient can be washed via the third flushing tube 301, thereby preventing coagulation of the secretions of the oral cavity and other similar situations.

In order to conveniently perform the intubation on the patient with a gastric tube, the endotracheal tube is further provided with one channel for passage of the gastric tube. In the case of the intubation with the gastric tube, the channel is directly utilized for such intubation, that is, the gastric tube enters the patient's esophagus through the channel. Specifically, the endotracheal tube includes a silicone film 402, the silicone film 402 is formed integrally with the endotracheal tube body 101 and the pharyngeal suction catheter 103, and the silicone film 402 is connected with each of an outer side wall of the pharyngeal suction catheter 103 and an outer side wall of the endotracheal tube body 101. The silicone film 402, the outer side wall of the pharyngeal suction catheter 103 and the outer side wall of the endotracheal tube body 101 constitute a gastric tube tunnel through which the gastric tube can pass. The silicone film is located beside the pharyngeal suction catheter and behind the endotracheal tube body, and the cavity of the tunnel has a size sufficient for a conventional gastric tube to pass therethrough. An opening of one end of the gastric tube tunnel is distanced from the baffle by 4 cm, and an opening of the other end of the gastric tube tunnel protrudes out of the oral cavity of the patient. Furthermore, the opening of the gastric tube tunnel, which is adjacent to the entrance of the patient's esophagus, is designed to be tilted, so that when the patient is in a 30° lying position, the tip of the opening is directed toward the entrance of the esophagus, making the insertion of the gastric tube easier.

Since the oral cavity, the pharynx and the nose of a human body produce secretions at any time, it is necessary to suck the secretions at regular intervals, so as to prevent accumulation of the secretions. In view of this, the endotracheal tube further includes a humidity sensing device, and the humidity sensing device includes a connecting wire 401 and a humidity sensing electrode 403. The humidity sensing electrode 403 is disposed at the side wall of the front bent portion 201 and located beside the port of the front bent portion. One end of the connecting wire 401 is electrically connected with the humidity sensing electrode 403, and the other end of the connecting wire 401 protrudes out of the patient's oral cavity. The connecting wire is extended so as to be externally connected with a power supply connector. If the pharyngeal secretions are accumulated and thus make the electrode soaked, the humidity sensing electrode 403 triggers an alarm and feeds it back to an external device, so that a warning is send out to inform a nursing staff or a suction apparatus is directly initiated, so as to achieve suction and removal of the pharyngeal secretions as needed. The humidity sensing electrode 403 and the suction device are both commercially available apparatuses, and thus are not described in detail.

The endotracheal tube with a pharyngeal suction catheter provided in the embodiments of the present disclosure has the following advantages:

1. The endotracheal tube body and the pharyngeal suction catheter are integrally formed, and the pharyngeal suction catheter is placed along with the insertion of the endotracheal intubation, which enables the pharyngeal suction catheter to stay at the bottom of the pharynx of the patient for a long time; and moreover, the situation of constriction of the posterior pharyngeal wall is also avoided. As the pharyngeal suction catheter can stay at the bottom of the pharynx for a long time, the suction can be carried out flexibly and simply, reducing the discomfort of the patient that would otherwise be caused with a current conventional method which has to make a sputum suction tube repeatedly inserted into and withdrawn from the pharynx for suction, and avoiding injury and bleeding of mucosae of the oral cavity, the nose and pharynx of the patient as well as cross infection.

2. The front end of the pharyngeal suction catheter, that is, the front bent portion, is bent downward and rearward so that the end of the pharyngeal suction catheter is perpendicular to the endotracheal tube body, and the port of the pharyngeal suction catheter is designed to be distanced from the endotracheal tube body by 1.2 cm. After the endotracheal tube is successfully inserted, and when the patient is in a supine position with his/her head raised by 30 degrees, the suction catheter will be naturally close to the lowest part of the bottom of the pharynx, so that the secretions are removed more thoroughly. In addition, the port of the front bent portion is closed, and the suction ports are provided on the side wall of the front bent portion, and the suction ports are away from the end of the front bent portion by a certain distance; therefore, the situation that the mucosa is adsorbed by the suction ports during vacuum aspiration can be significantly reduced, thereby avoiding the problem of causing mucosal injury and bleeding during the suction of the secretions.

3. The front wall of the endotracheal tube is equipped with one flushing tube, and the pharyngeal suction catheter is designed with two flushing tubes. The three flushing tubes can be used cooperatively, which may keep the pharyngeal suction catheter unobstructed, contribute to the suction and removal of the secretions, and meanwhile, this may also keep the patient's oral cavity and pharynx clean, keep the mucosa moist, and prevent bonding of the secretions. The provision of the flushing tubes also makes it possible to flush and decontaminate areas around the glottis (including the gap above the balloon) as well as the oral cavity and the pharynx under a state that the suction is kept.

4. The soft silicone baffle is provided on the endotracheal tube body at a position adjacent to the balloon, to prevent oral secretions from flowing into the glottis along the endotracheal tube body. In addition, the suction ports of the pharyngeal suction catheter can also be positioned at the bottom of the pharynx.

5. With a timing switch or installation of a humidity sensing device, automatic suction is performed regularly or as needed, thereby greatly improving the efficiency of removal of pharyngeal secretions and significantly reducing the nursing workload.

6. The design of the gastric tube tunnel enables the gastric tube to be inserted more easily, and there is no need to suspend the gastric tube in the nostril, thereby reducing the incidence of discomfort of the nasal cavity, mucosal injury and bleeding as well as sinusitis.

The above description is merely illustrative of embodiments of the present disclosure and is not intended to limit the present disclosure. It would be understood by those skilled in the art that various modifications and variations can be made to the present disclosure. Any modifications, equivalent alternatives, improvements and so on made within the spirit and principle of the present disclosure are to be embraced in the scope of protection of the present disclosure.

The invention claimed is:

1. An endotracheal tube with a pharyngeal suction catheter, comprising:
   a baffle, an endotracheal tube body and a pharyngeal suction catheter, with the pharyngeal suction catheter configured for sucking and removing pharyngeal secretions from a patient, the baffle being sleeved onto one end of the endotracheal tube body, wherein the baffle is located above a balloon of the endotracheal tube body, wherein the endotracheal tube body is formed integrally with the pharyngeal suction catheter, and the pharyngeal suction catheter is connected with an outer wall of the endotracheal tube body and fixed directly behind the endotracheal tube body, the baffle is of a circular ring shape and extends in a direction away from the endotracheal tube body, one end of the pharyngeal suction catheter, which is adjacent to the baffle, is bent arcuately downward and rearward in a direction away from the endotracheal tube body to form a front bent portion, the front bent portion is close to the baffle in a direction from the baffle to the balloon, an end of the front bent portion is closed, and a side wall of the front bent portion is provided with two suction ports,
   wherein the baffle is located at a position higher than a balloon of the endotracheal tube body by 3.5 cm, and the front bent portion is perpendicular to the endotracheal tube body, the end of the front bent portion is distanced from the endotracheal tube body by 1.2 cm, and an end of the front bent portion is flush with a level line of the baffle.

2. The endotracheal tube with a pharyngeal suction catheter of claim 1, wherein the endotracheal tube further comprises a first flushing tube, the first flushing tube is embedded in a front wall of the endotracheal tube body, one end of the first flushing tube is provided with an opening, with the opening toward an outside of the endotracheal tube body and distanced from the baffle by 1.5 cm, the first flushing tube runs along with the endotracheal tube body to go beyond an incisor line, and is separated, after being away from the incisor line by 3.0 cm, from the endotracheal tube body, and the first flushing tube is extended so as to be externally connected with a syringe connector.

3. The endotracheal tube with a pharyngeal suction catheter of claim 1, wherein one end of the pharyngeal suction catheter is located adjacent to the baffle, the pharyngeal suction catheter runs along with the endotracheal tube body and is separated, at a position lower than an incisor line by 3.5 cm, from the endotracheal tube body, and the pharyngeal suction catheter is extended so as to be externally connected with a hose connector.

4. The endotracheal tube with a pharyngeal suction catheter of claim 2, wherein the two suction ports are symmetrically distributed along an axial direction of the pharyngeal suction catheter, and both of the suction ports are distanced from the end of the front bent portion by 3 mm.

5. The endotracheal tube with a pharyngeal suction catheter of claim 4, wherein the endotracheal tube further comprises a second flushing tube, the second flushing tube is embedded in a front wall of the pharyngeal suction catheter connected with the endotracheal tube body, an opening of one end of the second flushing tube is disposed in a catheter cavity and located below and behind the suction ports on both sides, and the opening is close to the port of the pharyngeal suction catheter, the second flushing tube runs along with the pharyngeal suction catheter to go beyond an incisor line and is separated, after being away from the incisor line by 3.0 cm, from the pharyngeal suction catheter, and the second flushing tube is extended so as to be externally connected with a syringe connector.

6. The endotracheal tube with a pharyngeal suction catheter of claim 4, wherein the endotracheal tube further comprises a humidity sensing device, the humidity sensing device comprises a connecting wire and a humidity sensing electrode, the humidity sensing electrode is disposed at the side wall of the front bent portion and located beside the port of the front bent portion, one end of the connecting wire is electrically connected with the humidity sensing electrode, and the other end of the connecting wire protrudes out of an oral cavity of the patient.

7. The endotracheal tube with a pharyngeal suction catheter of claim 5, wherein the endotracheal tube further comprises a third flushing tube, the third flushing tube is embedded in a rear tube wall of the pharyngeal suction catheter, one end of the third flushing tube directly faces a top of a hard palate of the patient after successful intubation of the patient, and the one end of the third flushing tube is provided with an opening, with the opening toward outside of the rear tube wall, the third flushing tube runs along with the pharyngeal suction catheter to go beyond an incisor line and is separated, after being away from the incisor line by 3.0 cm, from the pharyngeal suction catheter, and the third flushing tube is extended so as to be externally connected with a syringe connector.

8. The endotracheal tube with a pharyngeal suction catheter of claim 1, wherein the endotracheal tube further comprises a silicone film formed integrally with the endotracheal tube body and the pharyngeal suction catheter, the silicone film is connected with each of an outer side wall of the pharyngeal suction catheter and an outer side wall of the endotracheal tube body, the silicone film, the outer side wall of the pharyngeal suction catheter and the outer side wall of the endotracheal tube body constitute a gastric tube tunnel through which a gastric tube can pass, the silicone film is located beside the pharyngeal suction catheter and behind the endotracheal tube body, a tunnel cavity of the gastric tube tunnel has a size sufficient such that a conventional gastric tube can pass through, an opening of one end of the gastric tube tunnel is distanced from the baffle by 4.0 cm, and an opening of the other end of the gastric tube tunnel protrudes out of an oral cavity of the patient.

9. The endotracheal tube with a pharyngeal suction catheter of claim 2, wherein the front bent portion is perpendicular to the endotracheal tube body, the end of the front bent portion is distanced from the endotracheal tube body by 1.2 cm, and an end of the front bent portion is flush with a level line of the baffle.

10. The endotracheal tube with a pharyngeal suction catheter of claim 3, wherein the front bent portion is perpendicular to the endotracheal tube body, the end of the front bent portion is distanced from the endotracheal tube body by 1.2 cm, and an end of the front bent portion is flush with a level line of the baffle.

11. The endotracheal tube with a pharyngeal suction catheter of claim 1, wherein the endotracheal tube further comprises a third flushing tube, the third flushing tube is embedded in a rear tube wall of the pharyngeal suction catheter, one end of the third flushing tube directly faces a top of a hard palate of the patient after successful intubation of the patient, and the one end of the third flushing tube is provided with an opening, with the opening toward outside of the rear tube wall, the third flushing tube runs along with the pharyngeal suction catheter to go beyond an incisor line and is separated, after being away from the incisor line by 3.0 cm, from the pharyngeal suction catheter, and the third flushing tube is extended so as to be externally connected with a syringe connector.

12. The endotracheal tube with a pharyngeal suction catheter of claim 2, wherein the endotracheal tube further comprises a third flushing tube, the third flushing tube is embedded in a rear tube wall of the pharyngeal suction catheter, one end of the third flushing tube directly faces a top of a hard palate of the patient after successful intubation of the patient, and the one end of the third flushing tube is provided with an opening, with the opening toward outside of the rear tube wall, the third flushing tube runs along with the pharyngeal suction catheter to go beyond the incisor line and is separated, after being away from the incisor line by 3.0 cm, from the pharyngeal suction catheter, and the third flushing tube is extended so as to be externally connected with a syringe connector.

13. The endotracheal tube with a pharyngeal suction catheter of claim 3, wherein the endotracheal tube further comprises a third flushing tube, the third flushing tube is embedded in a rear tube wall of the pharyngeal suction catheter, one end of the third flushing tube directly faces a top of a hard palate of the patient after successful intubation of the patient, and the one end of the third flushing tube is provided with an opening, with the opening toward outside of the rear tube wall, the third flushing tube runs along with the pharyngeal suction catheter to go beyond the incisor line and is separated, after being away from the incisor line by 3.0 cm, from the pharyngeal suction catheter, and the third flushing tube is extended so as to be externally connected with a syringe connector.

* * * * *